United States Patent
Friesenhagen et al.

(10) Patent No.: US 7,169,749 B1
(45) Date of Patent: Jan. 30, 2007

(54) METHOD FOR PRODUCING ALKYL-SUBSTITUTED BUTENOLS

(75) Inventors: Lothar Friesenhagen, Duesseldorf (DE); Stephan Heck, Pulheim (DE); Norbert Klein, Mettmann (DE); Thomas Markert, Monheim (DE); Gerrit Pelzer, Duesseldorf (DE); Markus Schneider, Duisburg (DE)

(73) Assignee: Kao Corporation, Tokyo (JP)

( * ) Notice: Subject to any disclaimer, the term of this patent is extended or adjusted under 35 U.S.C. 154(b) by 230 days.

(21) Appl. No.: 10/088,385

(22) PCT Filed: Sep. 8, 2000

(86) PCT No.: PCT/EP00/08772

§ 371 (c)(1), (2), (4) Date: Aug. 12, 2002

(87) PCT Pub. No.: WO01/21568

PCT Pub. Date: Mar. 29, 2001

(30) Foreign Application Priority Data

Sep. 17, 1999 (DE) ................ 199 44 524

(51) Int. Cl.
*C07C 27/22* (2006.01)

(52) U.S. Cl. .............. 512/25; 568/700; 568/840; 568/876; 568/878; 568/880; 568/881; 568/884; 568/885

(58) Field of Classification Search .......... 512/25; 568/700, 840, 876, 878, 880, 881, 884, 885
See application file for complete search history.

(56) References Cited

U.S. PATENT DOCUMENTS 4,072,720 A * 2/1978 Haag et al. ............ 568/814

5,364,986 A 11/1994 Demmering et al.

FOREIGN PATENT DOCUMENTS

| DE | 42 42 466 A1 | 6/1994 |
|---|---|---|
| DE | 195 20 103 A1 | 12/1996 |
| EP | 0 829 463 A2 | 3/1998 |
| JP | 55/036423 A | 3/1980 |

OTHER PUBLICATIONS

E.T. Morris, "Aus der faszinierenden Naturgeschichte des Sandelholzes", Dragoco Report, 30, (1983), pp. 40-47.
B.M. Lawrence, B.D. Mookherjee, B.J. Willis (Eds.): "Flavors and Fragrances: A World Perspective", Elsevier Publishers, Amsterdam (1988)—(reciting entire book—not included).

* cited by examiner

*Primary Examiner*—Monique T. Cole
(74) *Attorney, Agent, or Firm*—Oblon, Spivak, McClelland, Maier & Neustadt, P.C.

(57) ABSTRACT

Alkyl-substituted butenols having the formula (I):

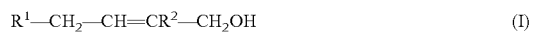

$$R^1—CH_2—CH=CR^2—CH_2OH \qquad (I)$$

wherein $R^1$ is a saturated or olefinically unsaturated alkyl or cycloalkyl group having from 4 to 16 carbon atoms and wherein $R^1$ is optionally substituted by an alkyl, cycloalkyl, aryl or alkaryl having up to 12 carbon atoms; $R^2$ is hydrogen or an alkyl group having from 1 to about 6 carbon atoms are produced by a process which comprises: (1) reacting an aldehyde of the formula (II):

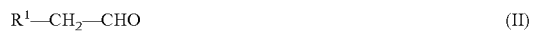

$$R^1—CH_2—CHO \qquad (II)$$

wherein $R^1$ has the same meaning as in formula (I), with the corresponding lower aldehyde to form an unsaturated aldehyde in an inert organic solvent; (2) continuously contacting an optionally calcined copper/zinc catalyst with the unsaturated aldehyde under isothermal conditions at temperatures of from about 45 to about 60° C. and under a hydrogen pressure of from 1 to about 300 bar.

17 Claims, No Drawings

METHOD FOR PRODUCING ALKYL-SUBSTITUTED BUTENOLS

BACKGROUND OF THE INVENTION

This invention relates to a process for the production of alkyl-substituted butenols by reduction of the corresponding aldehyde precursor in the presence of copper/zinc catalysts, the process being carried out continuously under isothermal conditions in a narrow temperature range.

PRIOR ART

Judging by demand, the availability of many natural perfumes is totally inadequate. From the perfumistic point of view, sandalwood oil is rated particularly highly and is of great value. It is obtained by steam distillation from the heartwood of the sandalwood tree, a tropical semiparasite which occurs in India and Malaysia. Heartwood appears after about 10 years and only begins to develop relatively quickly in 20-year-old trees. Fully grown trees are uprooted at the age of 30 to 60 because the roots are particularly rich in fragrant heartwood [cf. E. T. Morris, Dragoco Report 1983 (30), 40]. It will therefore be appreciated why perfume researchers are constantly endeavoring to develop suitable substitutes for natural sandalwood oil.

The focal points in the development of suitable substitutes for natural sandalwood oil were outlined by R. E. Naipawer in a review [in: B. M. Lawrence, B. D. Mookherjee, B. J. Willis (Eds.): "Flavors and Fragrances: A World Perspective", Elsevier Publishers, Amsterdam 1988]. In this review, it is mentioned inter alia that, since the middle of the seventies, campholenyl derivatives have played an important part as synthetic perfumes with a sandalwood perfume. A key role in this access to synthetic sandalwood perfumes has been played by the fact that campholene aldehyde (B), the synthesis building block on which the compounds mentioned are based, can readily be obtained from α-pinene, a natural substance.

2-Alkyl-4-(2,2,3-trimethylcyclopent-3-enyl)-but-2-en-1-ols (A), hereinafter referred to as sandalols, are sought-after perfumes with a pronounced sandalwood fragrance.

$$CY-CH_2-CH=CR-CH_2OH \quad (A)$$

CY=4-(2,2,3-trimethylcyclopent-3en-1-yl) group

R=H or $C_{1-6}$ alkyl

JP-A2-55/036423 (reported in Chem. Abstr. 93/094886p) describes a process for the production of such a sandalol in which α-campholene aldehyde (B) is reacted with propionaldehyde ($CH_3-CH_2-CHO$) in the presence of sodium hydroxide as basic catalyst.

$$Cy-CH_2CHO \quad (B)$$

Cy=4-(2,2,3-trimethylcyclopent-3-en-1-yl) group

The unsaturated aldehyde (C) formed in this mixed aldol condensation was isolated in a yield of 73.5%.

$$Cy-CH_2-CH=C(CH_3)-CHO \quad (A)$$

Cy=4(2,2,3-trimethylcyclopent-3-en-1-yl) group

Finally, in another step, this unsaturated aldehyde (C) was reduced with $Al[OCH(CH_3)]_3$ to form the corresponding sandalol (A). The yield obtained is put at 85%.

DE-A-195 20 103 describes a process for the production of alkyl-substituted butenols where unsaturated aldehydes are prepared by aldol condensation in a first step and are subsequently reduced in the presence of an optionally calcined copper/zinc catalyst. Example 3 of this application (page 5, lines 5 to 26), which describes the second stage of the process (reduction step), refers to batch operation and a reaction temperature of 160° C.

Continuous operation in an extremely narrow and relatively low temperature range is neither disclosed nor suggested in DE-A-195 20 103. Isothermal operation is also not mentioned in DE-A-195 20 103.

DESCRIPTION OF THE INVENTION

The known processes for the production of sandalols (A) are not entirely satisfactory in regard to yield and economy. Accordingly, there was a need for an improved process for the production of the compounds (A) and analogous compounds where the "Cy" group would be replaced by another saturated or olefinically unsaturated, optionally substituted alkyl or cycloalkyl group. More particularly, there was a need to ensure that the nonspecific formation of numerous secondary products would largely be avoided. Secondary products in a perfumistic context are understood to be worthless or even troublesome products.

It has now been found that alkyl-substituted butenols corresponding to general formula (I):

$$R^1-CH_2-CH=CR^2-CH_2OH \quad (I)$$

in which $R^1$ is a saturated or olefinically unsaturated alkyl or cycloalkyl group containing 4 to 16 carbon atoms which may optionally be substituted by an alkyl, cycloalkyl, aryl or alkaryl group, with the proviso that this substituent contains at most 12 carbon atoms, and $R^2$ is hydrogen or an alkyl group containing 1 to 6 carbon atoms, can be produced in high yields providing the aldol condensation of aldehydes corresponding to formula (II):

$$R^1-CH_2-CHO \quad (II)$$

in which $R^1$ has the same meaning as in formula (I), and the corresponding lower aldehyde is carried out in an inert organic solvent and the unsaturated aldehydes obtained are reduced in the presence of an optionally calcined copper/zinc catalyst, the process being carried out continuously under isothermal conditions in a narrow temperature range.

Accordingly, the present invention relates to a process for the production of alkyl-substituted butenols corresponding to general formula (II):

$$R^1-CH_2-CH=CR^2-CH_2OH \quad (I)$$

in which $R^1$ is a saturated or olefinically unsaturated alkyl or cycloalkyl group containing 4 to 16 carbon atoms which may optionally be substituted by an alkyl, cycloalkyl, aryl or alkaryl group, with the proviso that this substituent contains at most 12 carbon atoms, and $R^2$ is hydrogen or an alkyl group containing 1 to 6 carbon atoms, by reacting aldehydes corresponding to formula (II):

$$R^1-CH_2-CHO \quad (II)$$

in which $R^1$ has the same meaning as in formula (I), with the corresponding lower aldehydes and subsequently reducing the unsaturated aldehydes obtained, i) the aldol condensation being carried out in an inert organic solvent and (ii) the reduction of the unsaturated aldehydes being carried out in the presence of an optionally calcined copper/zinc catalyst, with the proviso that the reduction in step ii) is carried out continuously under isothermal conditions at temperatures of 45 to 60° C. and under a hydrogen pressure of 1 to 300 bar.

The process according to the invention has the advantage over the prior art that intermediate products and valuable products are obtained in high purities and in substantially quantitative yields. In particular, it has the advantage that the valuable product (I) obtained in the hydrogenation step is formed with a very high chemical purity and selectivity. Of particular importance in this connection is the fact that unwanted secondary products, for example compounds derived from (I) of which the C=C double bonds are completely or partly hydrogenated, and unreacted aldehyde (from the aldol condensation), are formed in a distinctly reduced quantity by comparison with processes where the features to be observed in accordance with the invention do not exist. This is particularly of advantage when the valuable product (I) obtained in the hydrogenation step is used as a raw material for the production of perfumes.

Step i)

Particularly suitable inert organic solvents for step i) are nonpolar solvents which form an azeotrope with water. Examples of suitable solvents are toluene, xylene, benzene, cyclohexane and methyl cyclohexane.

In a special embodiment of the invention, ammonium salts of an organic acid are used to catalyze the aldol condensation.

Propionaldehyde is preferably used in a 2.5- to 10-fold molar excess, based on the aldehyde (II). In one particular embodiment, propionaldehyde is used in a 2.5- to 3.5-fold molar excess.

As already mentioned, the aldol condensation is preferably carried out in the presence of an ammonium salt of an organic acid in the process according to the invention. Basically, the nature of the acid is not critical. Nor does it matter whether the ammonium salt is used as such or whether it is formed in situ during the reaction—for example from an amine and an organic acid. Examples of suitable ammonium salts are benzyl trimethyl ammonium hydroxide, piperidinyl acetate, pyrrolidinium acetate, ammonium acetate, dimethyl ammonium pyridinyl acetate, morpholine acetate, Lewatit 11600 (active with acetic acid), piperidinyl formate, N,N-tetraacetyl ethylenediamine, N,N-diacetyl ethylenediamine, dibutyl ammonium acetate and piperidinyl propionate. The concentration of the catalyst is preferably in the range from 0.001 to 20 mole-% and more particularly in the range from 0.5 to 10 mole-%, based on the aldehyde (II) used.

In another preferred embodiment of the present invention, $R^1$ in general formula (I) is a 4-(2,2,3-trimethylcyclopent-3-enyl) group.

Step ii)

The process according to the invention is carried out at temperatures of 45 to 60° C. In one particularly preferred embodiment, the reaction temperature is in the range from 50 to 55° C.

The process according to the invention is distinguished inter alia by the fact that, in step ii), it is carried out both continuously and isothermally.

Carrying out the process according to the invention continuously in step ii), which is preferably carried out in a fixed-bed reactor, ensures that the proportion of secondary products is small. The reason for this on the one hand is that, where this procedure is adopted, it is readily possible by controlling the volumetric flow rate of aldehyde or aldehyde and solvent to keep the reaction time short. On the other hand, the heterogeneous catalysis applied here ensures that the reaction product is not accompanied by significant quantities of the catalyst.

Carrying out the process isothermally means that no significant temperature gradients occur in the continuously operated reactor and that, in particular, there are no temperature peaks. By contrast, a nonisothermal reaction procedure would be characterized by the occurrence of distinct temperature gradients or temperature peaks in the reactor. Nonisothermal conditions usually prevail in batch hydrogenation, i.e. hydrogenation in an autoclave. In continuous operation, a nonisothermal reaction procedure would be characterized by the absence of special precautions to control the exothermy of the reaction.

To establish isothermal conditions, a particular embodiment of the process according to the invention is characterized in that the temperature is controlled by external jacket heating, for example with thermal oil, and/or the throughflow rate is adjusted to a correspondingly high level.

In particular, the throughflow rate in step ii) is adjusted to a value of 0.5 to 1.5 m$^3$/h and more particularly to a value of 0.8 to 1.2 m$^3$/h.

A preferred embodiment of the invention is characterized in that the copper/zinc catalyst is used in particulate form, i.e. the catalyst which is used in the reaction zone of the fixed-bed reactor is in the form of solid particles (heterogeneous catalyst). The particles may assume various sizes and shapes, for example tablets, lumps, cylinders, rods, rings. Basically, the size of the particles is not critical. However, it is normally adapted to the particular reactor dimensions present so that the liquid phase and the carrier gas are able to pass through the reaction zone unhindered and no unwanted drop in pressure occurs in that region. Typical suitable particle sizes range from a mean diameter of ca. 1 millimeter to ca. 10 millimeters although larger or smaller particle sizes are also possible.

A typical laboratory apparatus for carrying out the process according to the invention comprises a fixed-bed reactor of a double-jacketed tube. The inner tube contains the heterogeneous hydrogenation catalyst and acts as the reaction zone. The intermediate space is used for heating with a liquid medium. The aldehyde or the mixture of aldehyde and solvent can be delivered continuously to the reactor through heatable pipes by a controllable piston diaphragm pump. After leaving the reactor, the reaction products formed can readily be quantitatively removed via a cooling unit and an expansion system.

The typical technical equipment for carrying out the process according to the invention described with reference—by way of example—to a laboratory apparatus can readily be applied to correspondingly scaled up pilot-plant or production reactors. In principle, any of the usual tube or tube-bundle reactors may be used for this purpose.

So far as the hydrogen pressure is concerned, step ii) of the process is preferably carried out in the 200 to 300 bar range. Hydrogen pressures of 220 to 260 bar are particularly preferred.

The hydrogenation in step ii) is preferably carried out in the presence of a solvent. Alcoholic compounds, especially low molecular weight primary alkanols, such as methanol and/or ethanol, are particularly suitable solvents. The quantity ratio of aldehyde to solvent in step ii) of the process according to the invention is basically not critical although ratios by volume of aldehyde to solvent of 10:1 to 1:10 are preferred, a range of 3:1 to 1:1 being particularly preferred.

The copper/zinc catalysts to be used for the purposes of the invention are known from the prior art. They are prepared in accordance with DE-A-42 42 466 by adding alkali metal carbonate compounds to aqueous solutions containing water-soluble copper(II) and zinc(II) salts up to a pH value of 6 to 10, removing and drying the deposit formed, calcining the dried catalyst for 1 to 60 minutes at temperatures of 400 to 600° C. and then converting the calcined catalyst into particulate form. Further information on the production of the copper/zinc catalysts can be found in DE-A-42 42 466, page 3, lines 13 to 34.

In order substantially to avoid further hydrogenation of the target product (I) to secondary products, it has proved to be favorable in the continuous reaction in a fixed-bed reactor to adjust the volumetric flow rate of the aldehyde to LHSV values which are preferably in the range from 0.3 to 3.0 $h^{-1}$ and more particularly in the range from 0.6 to 1.2 $h^{-1}$. The LHSV value (liquid hourly space velocity) is understood from the literature to be the volumetric flow rate of the liquid, based on the volume of the solid catalyst. The LHSV values mentioned herein are based solely on the aldehyde, i.e. the solvent optionally used is disregarded.

The circulating gas volume is adjusted to values of 1 to 2 $Dm^3/h$ ("pressure cubic meters per hour"). By circulating gas volume is meant: $m^3$ circulating gas per hour for a reactor pressure of 250 to 300 bar. This parameter is measured in the pressure range of the reactor used (cf. Example 3 of the present application and the associated FIG. 1) after the gas circulation pump by means of a turbine.

For the purposes of the invention, the volumetric flow rate is normally adjusted to GHSV values in the range from 200 to 1,000 $h^{-1}$ and preferably to GHSV values in the range from 250 to 500 $h^{-1}$. The GHSV value (gaseous hourly space velocity) is understood from the literature to be the volumetric flow rate of the carrier gas, based on the volume of the solid catalyst.

EXAMPLES

1. Substances Used

1.1. For the Aldol Condensation

α-campholene aldehyde: 85% (Glidco)

propionaldehyde: 98% (Riedel-de-Häen)

KF on $Al_2O_3$: 240 g basic aluminium oxide were suspended in 320 g of a 50% aqueous potassium fluoride solution and then concentrated to dryness in a water jet vacuum in a rotary evaporator. The catalyst was then dried for 4 hours at 130° C./50 mbar.

1.2. For the Reduction of the Unsaturated Aldehyde

Copper/zinc catalyst: The copper/zinc catalyst used was prepared in accordance with Example A) of DE-A-42 42 466 using copper(II) nitrate trihydrate, zinc(II) nitrate hexahydrate and sodium carbonate.

2. The Reactions

2.1. Aldol Condensation

Example 1

Quantities Used:

3.04 g (20 moles) α-campholene aldehyde 4.64 kg (80 moles) propionaldehyde 400 g basic aluminium oxide charged with 40% potassium fluoride.

Reaction Procedure:

1.5 kg of a mixture (molar ratio 1:4) of campholene aldehyde and propionaldehyde was introduced into a 10-liter glass reactor. 400 kg of KF on $Al_2O_3$ were added in portions under nitrogen (5 l/h) with vigorous stirring and cooling, the temperature of the reaction mixture being kept between 40 and 50° C. The remaining 6.2 kg of the aldehyde mixture were then continuously added under nitrogen with vigorous stirring at a rate of 2 liters per hour. The reaction was exothermic and was kept by cooling at 40° C. After the addition, the mixture was stirred overnight at 50° C., the campholene aldehyde reacting off completely.

Working Up:

To remove the catalyst, the reaction mixture was pumped into a 2-liter pressure nutsche and filtered under 5 bar nitrogen. The filter cake was briefly washed with 0.5 liter of isopropanol. The crude product was returned to the reactor and ca. 270 g organic phase and 22 g water phase were distilled off at atmospheric pressure and at bottom temperatures of up to 150° C. The residue of 5.1 kg left in the reaction vessel was washed twice with 2 liters of saturated sodium sulfate solution. The residue of 5 kg remaining was further processed as a crude product (the content of 2-methyl-(2,2,3-trimethylcyclopent-3-en-1-yl)-but-2-en-1-al was found by gas chromatography to be 43%).

Example 2

Quantities Used:

3.04 kg (20 moles) α-campholene aldehyde 2.9 kg (50 moles) propionaldehyde

170+85 g (3 moles) piperidine

120+60 g (3 moles) glacial acetic acid 2 kg toluene

Reaction Procedure:

3.04 kg of campholene aldehyde and 2 kg of toluene were introduced into a 10-liter glass reactor and 2.9 kg of propionaldehyde, 170 g of piperidine and 120 g of glacial acetic acid were added with stirring at room temperature. The mixture was then refluxed for 4 hours on a water separator, 680 ml of water of reaction being removed from the circuit. Analysis of a sample of the reaction mixture by gas chromatography revealed a percentage content of 15% of unreacted educt. Accordingly, another 85 g of piperidine and 60 g of glacial acetic acid were added. After refluxing for another hour, another 120 g of water were removed from the circuit and the educt was completely reacted.

Working Up:

After 1.9 kg of toluene had been distilled off, the reaction mixture was washed twice with 2 liters of water. The organic phase of 6.24 kg was distilled in a 30 cm packed column (boiling point 88–102° C./0.1 mbar), 3.27 kg of a yellowish colored product (gas-chromatographic purity 85%) being obtained (85% of the theoretical).

2.2. Reduction

Example 3

Invention

Apparatus:

A jacketed high-pressure reactor filled with a Cu/Zn catalyst was used. It was connected to the following units: high-pressure product pump, heater, cooler, separator and gas circulation pump. The heat carrier circuit was controlled by a temperature-controllable apparatus. The layout of the apparatus used in schematized in FIG. 1.

LIST OF REFERENCE NUMERALS IN FIG. 1

1 educt (crude product of the aldol condensation of Example 2)/methanol
2 high-pressure product pump
3 heater
4 reactor (jacketed)
5 heat carrier oil
6 cooler
7 separator
8 gas circulation pump
9 hydrogen supply ("fresh $H_2$")

Quantities Used:

24.7 kg crude product of the aldol condensation of Example 2 (=educt)

10.5 kg methanol, technical quality (=solvent)

26 kg Cu/Zn catalyst

Reaction Procedure:

After it had been filled with the catalyst, the reactor was closed and tested for leaks with 250 bar hydrogen pressure. The catalyst was then activated by continuous introduction of hydrogen under a reactor pressure of 50 bar $N_2$ and at a temperature increased by 5° C. per hour, a final temperature of 200° C. being established. The circulating gas volume was kept at 1.5 $Dm^3/h$. The end of activation of the catalyst, as reflected in an $H_2$ content in the circulating gas of more than 5%, i.e. the catalyst did not take up any more hydrogen, was followed by gas exchange in the reactor. To carry out the hydrogenation process, 250 bar hydrogen was introduced into the reactor after the complete expansion of hydrogen and the catalyst bed was adjusted to 50–55° C. through the hydrogen, reactor entry and heat carrier temperature. The circulating gas volume was 2 $Dm^3/h$. After the operating parameters had stabilized, the addition of a mixture of 2 parts by volume of the crude product of the aldol condensation of Example 2 (=educt) and 1 part by volume of methanol (=solvent) was started at 10 l/h, rising gradually to 40 l/h. After all the mixture had been added, the educt/hydrogen mixture showed a reactor entry temperature and heat carrier oil exit temperature of 55° C. The exothermy in the reactor was 5 to 10° C. After cooling, the hydrogenation product and the hydrogen were separated in a separator, the hydrogen was fed to the gas circulation pump and the end product was removed through an automatic expansion system. The crude product obtained in this way was then characterized by gas chromatography. It contained 86% of the required valuable product, 12% of a perfumistically attractive accompanying product and 1.8% of unreacted educt. Hardly any of the secondary products formed, for example, at higher temperatures or in batch operation were detected.

The invention claimed is:

1. A process for the production of an alkyl-substituted butenol having the formula (I):

$$R^1—CH_2—CH=CR^2—CH_2OH \qquad (I)$$

wherein $R^1$ is a saturated or olefinically unsaturated alkyl or cycloalkyl group having from 4 to 16 carbon atoms and wherein $R^1$ is optionally substituted by an alkyl, cycloalkyl, aryl or alkaryl having up to 12 carbon atoms; and $R^2$ is hydrogen or an alkyl group having from 1 to about 6 carbon atoms the process comprising:
by reacting at least one aldehyde of the formula (II) with at least one corresponding lower aldehyde:

$$R^1—CH_2—CHO \qquad (II)$$

and $R^1$ has the same meaning as in formula (I);
wherein:
(i) aldol condensation is carried out in an inert organic solvent, and
(ii) reduction of the unsaturated aldehydes is carried out in the presence of an optionally calcined copper/zinc catalyst, and is carried out continuously under isothermal conditions at a temperature ranging from 45 to 60° C. and under a hydrogen pressure of 1 to 300 bar at an LHSV (liquid hourly space velocity) of 0.3 to 3.0 $hr^{-1}$.

2. The process of claim 1, wherein the aldol condensation is carried out in a nonpolar organic solvent which can form an azeotrope with water.

3. The process of claim 1, wherein the aldol condensation is carried out in the presence of a catalyst which is an ammonium salt of an organic acid.

4. The process of claim 1, wherein $R^2$ in formula (I) is a methyl group.

5. The process of claim 1, wherein $R^2$ in formula (I) is a methyl group and wherein propionaldehyde is used in a 2.5 to 10-fold molar excess based on the aldehyde of formula (II).

6. The process of claim 5, wherein the propionaldehyde is used in a 2.5 to 3.5-fold molar excess based on the aldehyde of formula (II).

7. The process of claim 1 wherein $R^1$ is a 4-(2,2,3-trimethylcyclopent-3-en-1-yl) group.

8. The process of claim 1, wherein the organic solvent in (i) is selected from the group consisting of toluene, xylene, benzene, cyclohexane and methyl cyclohexane.

9. The process of claim 1, wherein $R^1$ is a saturated alkyl group having from 4 to 16 carbon atoms.

10. The process of claim 1, wherein $R^1$ is an olefinically unsaturated alkyl group having from 4 to 16 carbon atoms.

11. The process of claim 1, wherein $R^1$ is an olefinically unsaturated cycloalkyl group having from 4 to 16 carbon atoms.

12. The process of claim 1, wherein $R^1$ is not further substituted.

13. The process of claim 1, wherein $R^1$ is substituted by an alkyl, cycloalkyl, aryl or alkaryl having up to 12 carbon atoms.

14. The process of claim 1, wherein $R^2$ is hydrogen.

15. The process of claim 1, wherein $R^2$ is an alkyl group having from 2 to 6 carbon atoms.

16. The process of claim 1, wherein said LHSV (liquid hourly space velocity) ranges from 0.6 to 1.2 $hr^{-1}$.

17. A process for the production of an alkyl-substituted butenol having the formula (I):

$$R^1—CH_2—CH=CR^2—CH_2OH \qquad (I)$$

wherein $R^1$ is a saturated or olefinically unsaturated alkyl or cycloalkyl group having from 4 to 16 carbon atoms and wherein $R^1$ is optionally substituted by an alkyl, cycloalkyl, aryl or alkaryl having up to 12 carbon atoms; and $R^2$ is hydrogen or an alkyl group having from 1 to about 6 carbon atoms the process comprising:
by reacting at least one aldehyde of the formula (II) with at least one corresponding lower aldehyde:

$$R^1—CH_2—CHO \qquad (II)$$

and R$^1$ has the same meaning as in formula (I);
wherein:
(i) aldol condensation is carried out in an inert organic solvent, and
(ii) reduction of the unsaturated aldehydes is carried out in the presence of an optionally calcined copper/zinc catalyst, and
is carried out continuously in a fixed bed reactor at a LHSV (liquid hourly space velocity) of 0.3 to 3.0 hr$^{-1}$, under isothermal conditions at a temperature ranging from 45 to 60° C., and
under a hydrogen pressure of 1 to 300 bar.

* * * * *